(12) United States Patent
Mahieu et al.

(10) Patent No.: US 7,540,376 B2
(45) Date of Patent: Jun. 2, 2009

(54) CONTACT LENS CASE

(75) Inventors: Frans Mahieu, Alpharetta, GA (US); Lynn Goldblatt, Atlanta, GA (US); Kim Muenzer, La Canada, CA (US); Spencer MacKay, Agoura Hills, CA (US)

(73) Assignee: Novartis AG, Basel (CH)

( * ) Notice: Subject to any disclaimer, the term of this patent is extended or adjusted under 35 U.S.C. 154(b) by 528 days.

(21) Appl. No.: 10/969,255

(22) Filed: Oct. 20, 2004

(65) Prior Publication Data

US 2005/0087453 A1    Apr. 28, 2005

Related U.S. Application Data

(60) Provisional application No. 60/513,289, filed on Oct. 22, 2003, provisional application No. 60/558,523, filed on Apr. 1, 2004, provisional application No. 60/584,030, filed on Jun. 30, 2004.

(51) Int. Cl.
*A45C 11/04* (2006.01)

(52) U.S. Cl. ........................ 206/5.1; 220/324

(58) Field of Classification Search ................ 206/5.1, 206/6, 210, 438; 215/237, 230; 220/324, 220/836, 840, 843, 845
See application file for complete search history.

(56) References Cited

U.S. PATENT DOCUMENTS

| | | | | |
|---|---|---|---|---|
| 2,274,973 A | 3/1942 | Bryant | | 215/13 |
| 2,374,092 A | 4/1945 | Glaser | | 215/10 |
| 2,690,861 A | 10/1954 | Tupper | | 222/498 |
| 2,744,649 A | 5/1956 | Smith | | 215/100 |
| 2,940,589 A | 6/1960 | Silverman | | 206/5 |
| 2,949,203 A | 8/1960 | Berg | | 215/6 |
| 3,089,500 A | 5/1963 | Stalcup | | 134/156 |
| 3,124,240 A | 3/1964 | Croan | | 206/5 |
| 3,252,492 A | 5/1966 | Marchant | | 150/5 |
| 3,326,358 A | 6/1967 | Singleton | | 206/5 |
| D208,166 S | 7/1967 | Hueber et al. | | D57/1 |
| 3,339,047 A | 8/1967 | Rys et al. | | 200/153 |
| 3,394,717 A * | 7/1968 | Hollinger | | 134/137 |
| 3,804,233 A | 4/1974 | Gregg, Jr. | | 206/19.5 R |
| 3,877,598 A | 4/1975 | Hazard | | 215/224 |
| 3,927,782 A | 12/1975 | Edwards | | 215/100 |
| 3,966,076 A | 6/1976 | Kroger et al. | | 220/20 |
| 4,002,275 A | 1/1977 | Crowle et al. | | 222/543 |
| 4,036,357 A | 7/1977 | Czelen | | 206/5.1 |
| D246,896 S | 1/1978 | Plummer | | D9/100 |
| 4,195,728 A | 4/1980 | Cardamone | | 206/45.33 |

(Continued)

FOREIGN PATENT DOCUMENTS

DE    199 40 727    3/2001

(Continued)

*Primary Examiner*—David T Fidei
(74) *Attorney, Agent, or Firm*—Sheng-Hsin Hu; Robert Ambrose; Jian Zhou

(57) ABSTRACT

A contact lens case including a body or base portion with a pair of lens-receiving wells recessed therein, a cap or cover closable to form a substantially liquid-impermeable seal around the wells, and a latch or closure assembly engageable to secure the cover in its closed position. A compressible gasket around the wells assists in forming the seal with the cover. The wells include a primary bowl portion with a tapered secondary portion extending therefrom to assist in lens removal.

17 Claims, 5 Drawing Sheets

U.S. PATENT DOCUMENTS

| | | | | |
|---|---|---|---|---|
| 4,235,343 A | | 11/1980 | Thompson | 215/6 |
| 4,406,362 A | * | 9/1983 | Thomas et al. | 206/5.1 |
| 4,429,786 A | | 2/1984 | Hucal | 206/5.1 |
| 4,501,378 A | * | 2/1985 | Berfield | 220/324 |
| 4,563,186 A | | 1/1986 | Flynn et al. | 8/137 |
| 4,640,423 A | | 2/1987 | Mednis | 215/10 |
| D289,923 S | | 5/1987 | Hoogesteger | D24/9 |
| 4,700,729 A | | 10/1987 | Thaler | 134/139 |
| 4,721,124 A | | 1/1988 | Tuerkheimer et al. | 134/138 |
| 4,776,972 A | | 10/1988 | Barrett | 252/90 |
| 4,856,647 A | | 8/1989 | Dahne | 206/5.1 |
| 4,858,754 A | * | 8/1989 | Wright et al. | 206/5.1 |
| 4,905,819 A | | 3/1990 | Clements et al. | 206/5.1 |
| 4,909,382 A | | 3/1990 | Cuppari | 206/5.1 |
| 4,925,017 A | | 5/1990 | Jessen | 206/5.1 |
| 4,942,959 A | | 7/1990 | Sauber et al. | 206/5.1 |
| 4,951,811 A | | 8/1990 | Lines | 206/5 |
| 4,966,296 A | | 10/1990 | Farrell | 220/23.4 |
| 5,002,179 A | | 3/1991 | Dhala | 206/5.1 |
| 5,050,757 A | | 9/1991 | Hidding et al. | 220/23.83 |
| 5,065,875 A | | 11/1991 | Balavich | 215/10 |
| 5,085,330 A | | 2/1992 | Paulin | 215/6 |
| D328,246 S | | 7/1992 | Nottingham et al. | D9/520 |
| 5,127,517 A | | 7/1992 | Clements et al. | |
| 5,129,520 A | | 7/1992 | Gaspar | 206/534 |
| 5,129,999 A | | 7/1992 | Holland et al. | 204/131 |
| 5,174,534 A | | 12/1992 | Mitchell | 248/311.2 |
| 5,186,317 A | | 2/1993 | Ryder et al. | 206/5.1 |
| 5,211,299 A | | 5/1993 | Manfredonia | 215/11.1 |
| 5,312,014 A | | 5/1994 | Hamlin | 220/703 |
| 5,348,185 A | * | 9/1994 | Buckner et al. | 220/326 |
| 5,375,699 A | | 12/1994 | Amend | 206/5.1 |
| 5,383,550 A | * | 1/1995 | Tsao | 206/5.1 |
| 5,415,275 A | | 5/1995 | Girimont | 206/5.1 |
| D362,390 S | | 9/1995 | Weiler | D9/520 |
| D379,714 S | | 6/1997 | Cerny et al. | D3/264 |
| 5,647,481 A | | 7/1997 | Hundertmark et al. | 206/219 |
| D404,915 S | | 2/1999 | Kornick et al. | D3/264 |
| D405,260 S | | 2/1999 | Kornick et al. | D3/264 |
| 6,073,757 A | | 6/2000 | Kornick et al. | 206/5.1 |
| 6,170,664 B1 | | 1/2001 | Dar | 206/511 |
| 6,289,906 B1 | | 9/2001 | Vanden Dries et al. | 134/117 |
| 6,536,453 B2 | | 3/2003 | Vanden Dries et al. | 134/117 |
| 2003/0010783 A1 | * | 1/2003 | Prezelin | 220/324 |
| 2003/0111476 A1 | * | 6/2003 | Serio, Jr. | 220/835 |
| 2005/0103656 A1 | * | 5/2005 | Jaron et al. | 206/303 |

FOREIGN PATENT DOCUMENTS

| | | |
|---|---|---|
| EP | 0 604 177 | 6/1994 |
| EP | 0 680 895 | 11/1995 |
| FR | 2 633 907 | 1/1990 |
| FR | 88609 | 10/1995 |
| WO | WO 93/20730 | 10/1993 |
| WO | WO 95/12995 | 5/1995 |
| WO | WO 95/26756 | 10/1995 |
| WO | WO 95/34231 | 12/1995 |

* cited by examiner

CONTACT LENS CASE

CROSS-REFERENCE TO RELATED APPLICATIONS

This application claims priority to U.S. Provisional Patent Application Ser. No. 60/513,289 filed Oct. 22, 2003, to U.S. Provisional Patent Application Ser. No. 60/558,523 filed Apr. 1, 2004, and to U.S. Provisional Patent Application Ser. No. 60/584,030 filed Jun. 30, 2004; which applications are hereby incorporated herein by reference in their entireties. Concurrently filed U.S. patent application Ser. No. 10/969,281 filed Oct. 20, 2004 is also incorporated herein by reference in its entirety.

TECHNICAL FIELD

This invention relates to improved cases for storage and care of contact lenses, and to related methods of contact lens storage and care.

BACKGROUND OF THE INVENTION

Contact lenses provide vision correction for many users. The advantages of contact lenses in comparison to spectacle glasses are numerous, including improved performance, convenience, and appearance. However, contact lenses typically require stringent care regimes in order to ensure comfort and avoid ocular infections. Proper care of contact lenses typically requires the consumer to periodically clean, disinfect, and/or rinse the lenses. Cleaning typically refers to removal of lipids, proteins or other matter, which has become affixed to a lens. Disinfecting typically refers to inactivating of harmful bacteria or fungi whenever the lenses are removed from the eye, which is usually on a daily basis. Cleaning typically occurs less frequently than disinfection, with a weekly cleaning regime being most common. Rinsing refers to removing cleaning or disinfecting solutions or debris from the lens before placing the lens in the eye.

Disinfecting, cleaning and/or rinsing of lenses often are accomplished by immersing a lens in an appropriate lens care solution (for example, a single- or multiple-purpose care solution) in a contact lens case. Such lens cases can also be used to store and transport contact lenses between use periods. When it is desired to treat contact lenses, the appropriate contact lens care composition is dispensed from a bottle or container into the contact lens case in which the contact lenses have been placed. Contact lenses are often left in a lens care solution in a lens case for an extended time, such as, for example, overnight or at least several hours. After treatment and rinsing, the contact lenses are ready for wear in the eyes of the user.

The care of contact lenses in this manner can be inconvenient, in that two separate containers (one being the container of lens care solution and the other being the lens case for treating and storing the lenses) are utilized. Because the solution container and the lens case are typically separate components, their organization and portability in-home and out-of-home can be challenging. For example, in in-home situations, separate shelf or counter space is typically required for organizing and storing these components. And during travel, one of the containers can quite easily be misplaced or forgotten. Numerous attempts at improving contact lens care systems have been proposed. For example, systems that combine a lens care solution bottle and a lens case have been suggested in U.S. Pat. Nos. 2,940,589, 3,326,358, 4,429,786, Des. 405,260, Des. 404,915, U.S. Pat. No. 6,536,453 and published PCT patent application No. WO 95/34231. However, problems and inconveniences remain with commercially available contact lens care systems in view of storage, portability, convenience and aesthetic appeal.

In addition, known contact lens cases for treating, storing and transporting lenses have been found to present a number of disadvantages. For example, some known lens cases have been found to be susceptible to leakage of the lens care solution, which can interfere with the cleaning and disinfecting of lenses, and allow lenses to dry out such that they become unsuitable for use when needed. Also, many known lens cases have been found to be inconvenient, cumbersome to open and close, and difficult to insert and remove contact lenses to and from their storage wells. And it has been found that many users prefer a lens case that can be opened and closed easily with one hand. In addition, it is generally preferable that a lens case provide secure closure and sealing to avoid leakage. It has also been found desirable to provide the user with some sensory feedback to confirm complete and proper closure.

Because many previously known lens cases are incapable of accomplishing such objectives it has been found that needs exist for an improved lens case for treatment, storage and transport of contact lenses. It is to the provision of an improved lens case meeting these and other needs that the present invention is primarily directed.

SUMMARY OF THE INVENTION

In preferred forms, the present invention is an improved lens case for treatment, storage and transport of contact lenses. In various example embodiments, the lens case of the present invention provides improved functionality in the handling and storage of lenses; and improved portability, convenience and aesthetic appeal to the customer. In addition, particular embodiments of the lens case of the present invention are compatible for use as part of an integrated lens care system wherein the lens case is configured for engagement into or onto a cooperating container of lens care solution, such that the user only needs to keep up with a single container.

The invention, in one aspect, is a contact lens case including a base portion defining at least one well for receiving a contact lens and a quantity of lens care solution. At least one cover is hingedly connected to the base portion and movable between an open position allowing access to the at least one well and a closed position overlying the at least one well. A latch is selectively engageable with a portion of the at least one cover to retain the cover in its closed position.

In another aspect, the invention is contact lens case including a main body portion having a well formed therein. The well preferably has a substantially hemispherical primary bowl portion and a secondary extension well portion extending from the primary bowl portion and having a progressively decreasing depth. The lens case preferably also includes a cap selectively closable over the well In still another aspect, the invention is a contact lens case including a base with a well formed therein. A cover is hingedly attached to the base and pivotal between an open position exposing the well and a closed position covering the well. A gasket is provided between the base and the cover, forming a fluid-impermeable seal around the well when the cover is in its closed position.

In another aspect, the invention is a contact lens case including a base having at least one well formed therein, at least one cover for closure over the at least one well, and closure means providing sensory confirmation indicating closure of the cover.

In another aspect, the invention is a contact lens case including a base having at least one well for receiving a contact lens and a quantity of lens care solution therein. A cover is hingedly mounted to the base and movable between a closed position and an open position. A lens carrier moves between a lowered position in the well when the cover is in its closed position, and a raised position above the well when the cover is in its open position.

In yet another aspect, the invention is a contact lens case having a base with first and second wells recessed therein, each well including a primary bowl portion and a secondary portion tapering to become progressively narrower and shallower away from the primary bowl portion. The lens case preferably also includes at least one cover hingedly connected to the base and pivotal between an open position allowing access to the first and second wells and a closed position covering the first and second wells. A compressible gasket is preferably provided between the base and the cover, the gasket providing a fluid-impermeable seal around the first and second wells when the cover is in its closed position. The lens case preferably also includes a closure member engageable to secure each of the at least one covers in its closed position.

The present invention, in another aspect, is a lens case configured for use in connection with an integrated lens care system, which includes a solution dispensing container having an openly accessible docking site for releasably securing the lens case. The lens case preferably includes one or more recesses, projections and/or other surface features for engagement with a cooperating element of the container docking site.

The present invention provides the foregoing and other features, and the advantages of the invention will become further apparent from the following detailed description of the example embodiments set forth herein, read in conjunction with the accompanying figures. The detailed description and figures are merely illustrative of the invention and do not limit the scope of the invention, which is defined by the appended claims and equivalents thereof.

DETAILED DESCRIPTION OF EXAMPLE EMBODIMENTS

Figure 1:
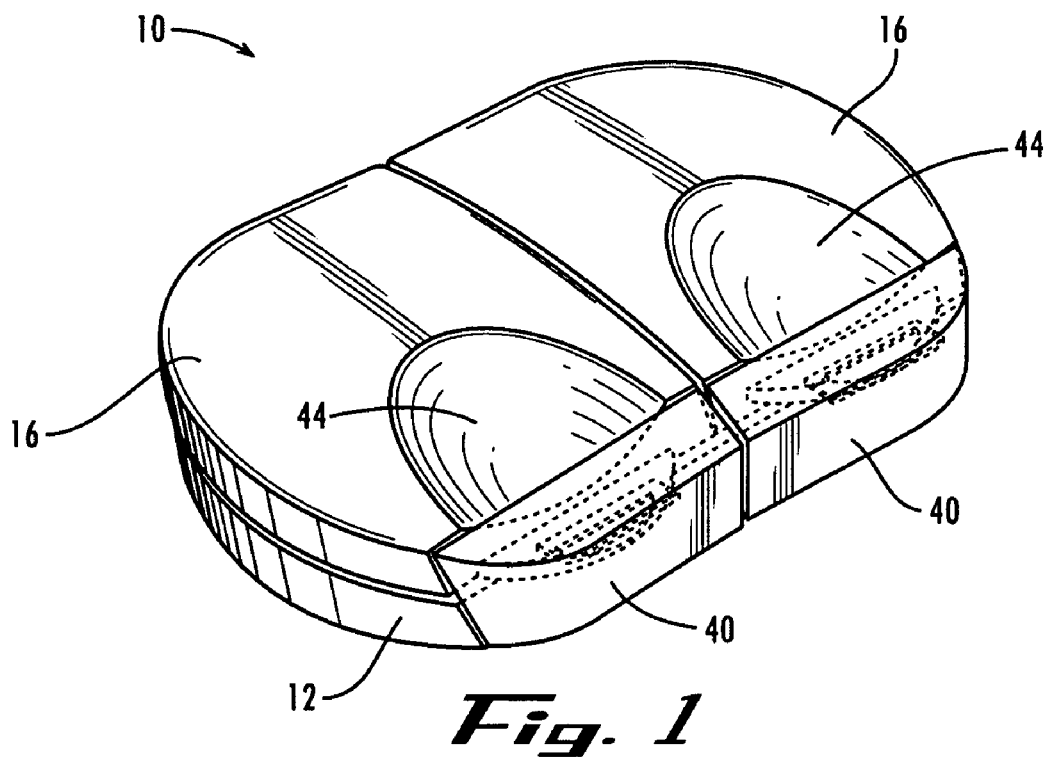
FIG. 1 is a perspective view of a lens case according to one example embodiment of the present invention, the case shown in a closed and latched configuration.

The present invention may be understood more readily by reference to the following detailed description of the invention taken in connection with the accompanying drawing figures, which form a part of this disclosure. Unless defined otherwise, all technical and scientific terms used herein have the same meaning as commonly understood by one of ordinary skill in the art to which this invention belongs. Generally, the nomenclature used herein is well known and commonly employed in the art. Conventional methods are used for carrying out the disclosed procedures, such as those provided in the art and various general references. It is to be understood that this invention is not limited to the specific devices, methods, conditions or parameters described and/or shown herein, and that the terminology used herein is for the purpose of describing particular embodiments by way of example only and is not intended to be limiting of the claimed invention. Also, as used in the specification including the appended claims, reference to singular forms such as "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

In various embodiments, the present invention is a lens case, preferably including a main body portion that includes a pair of separate and discrete wells or reservoirs, each adapted to receive one contact lens and a quantity of a lens care solution therein. Each well preferably comprises an open-faced recess or chamber in or on the main body portion, with a substantially circular, oval or rain-drop shaped periphery. Each well preferably comprises a smoothly-curved concave inner surface, and optionally also includes one or more slightly raised surface features (e.g., dots, lines, ridges, hills or lines radiating from the lowest point of each well) projecting from the inner surface to reduce the lens-contacting surface area and thereby reduce adhesion of a contact lens to the surface of the well.

One or two caps preferably are closable over the wells, so as to provide a substantially liquid-impermeable seal. The cap(s) preferably include a sealing rim or surface adapted to mate and seal with a compressible gasket surrounding the peripheries of the wells. Alternatively, the rim surrounds the wells and engages a compressible gasket on the cap(s) to seal the well's contents. In example embodiments, each cap is hingedly mounted to the main body of the case, and is adapted to be pivoted between an open position and a closed position. In other embodiments, each cap is separably attached to the main body of the case, as for example by means of threaded or snap-connection fittings. A latching or coupling assembly is preferably provided, which can be engaged and disengaged, preferably with one single manual action (and preferably with one hand), to positively secure the caps in their closed position and engage the seal. The coupling assembly preferably includes at least one member having a snap-fitting connection attached to the case main body or to the cap.

It is understood that a lens case of the invention can include a main body portion comprising a pair of wells which are merged together in a manner so that a pair of contact lenses in a side-by-side relationship can be held in the merged well. Each well preferably comprises an open-faced recess or chamber in or on the main body portion, with a substantially circular, oval or rain-drop shaped periphery. Each well preferably comprises a smoothly-curved concave inner surface, and optionally also includes one or more slightly raised surface features (e.g., dots, lines, ridges, hills or lines radiating from the lowest point of each well) projecting from the inner surface to reduce the lens-contacting surface area and thereby reduce adhesion of a contact lens to the surface of the well.

It is also understood that there can exist one or more liquid passage ways between the pair of wells so that a lens care solution can flow from one well to the other well.

The lens case is preferably constructed of a material that is sturdy and impervious to chemicals contained in typical lens care solutions. For example, polystyrene, high-density polyethylene, or polypropylene can be the construction material of choice, although others may be used. The shape of the contact lens case of the present invention preferably promotes consumer convenience and aesthetic appeal. For example, consumer convenience is preferably promoted by providing convenient ergonomic grasping surfaces for ease of opening and closing the case. The aesthetic appeal of the lens case is preferably promoted by providing the case with a smoothly contoured plan profile having a continuously curved periphery or cross-section.

With reference now to FIGS. 1-4, a first example embodiment of a lens case 10 according to the present invention is shown. The lens case 10 preferably comprises a main body portion or base 12, within which is formed at least one, and preferably a pair of separate and discrete wells 14, each adapted to receive one contact lens and an amount of a lens care solution. Each well 14 preferably comprises a concave recess or chamber having an open top face. The periphery of each well 14 preferably defines a teardrop or raindrop shaped profile having a generally circular primary well portion with a pointed extension portion projecting laterally from one side thereof. The main body portion or base 12 of the lens case preferably comprises an integral molding of plastic or other substantially rigid material of construction, and optionally comprises an antimicrobial surface treatment or material of construction.

Figure 2:
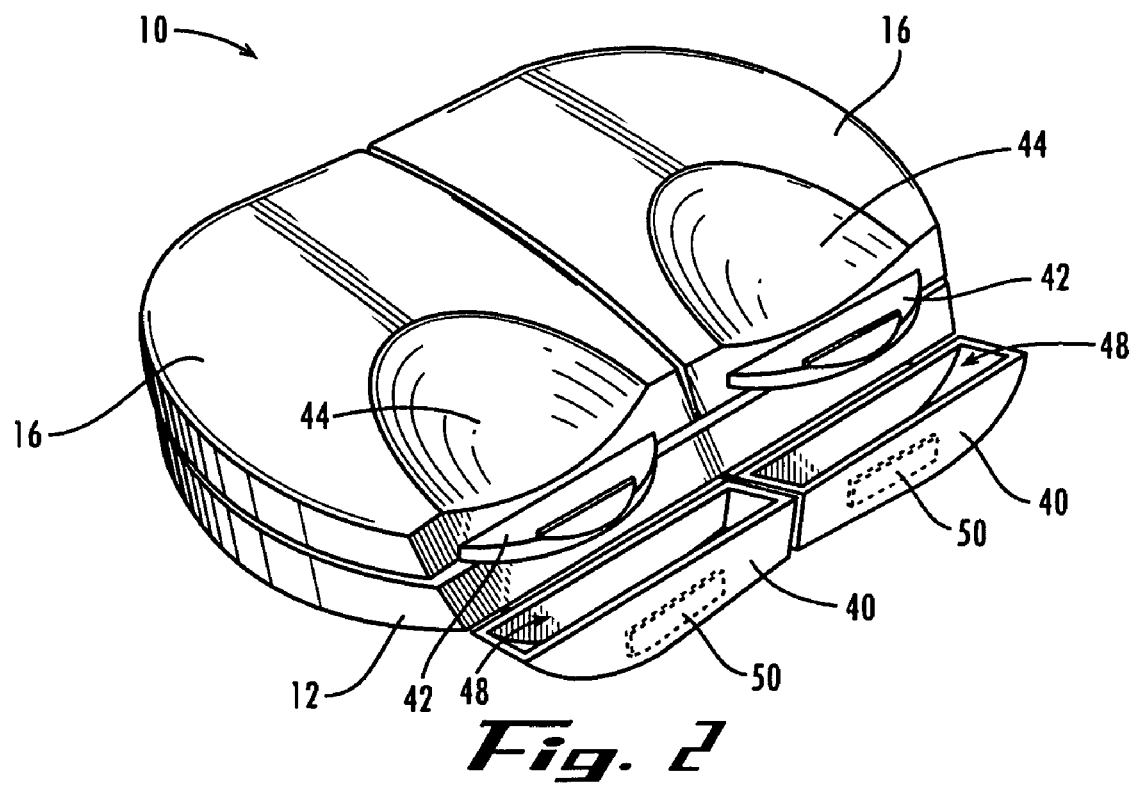
FIG. 2 shows the lens case of FIG. 1 in an unlatched and closed configuration.
Figure 3:
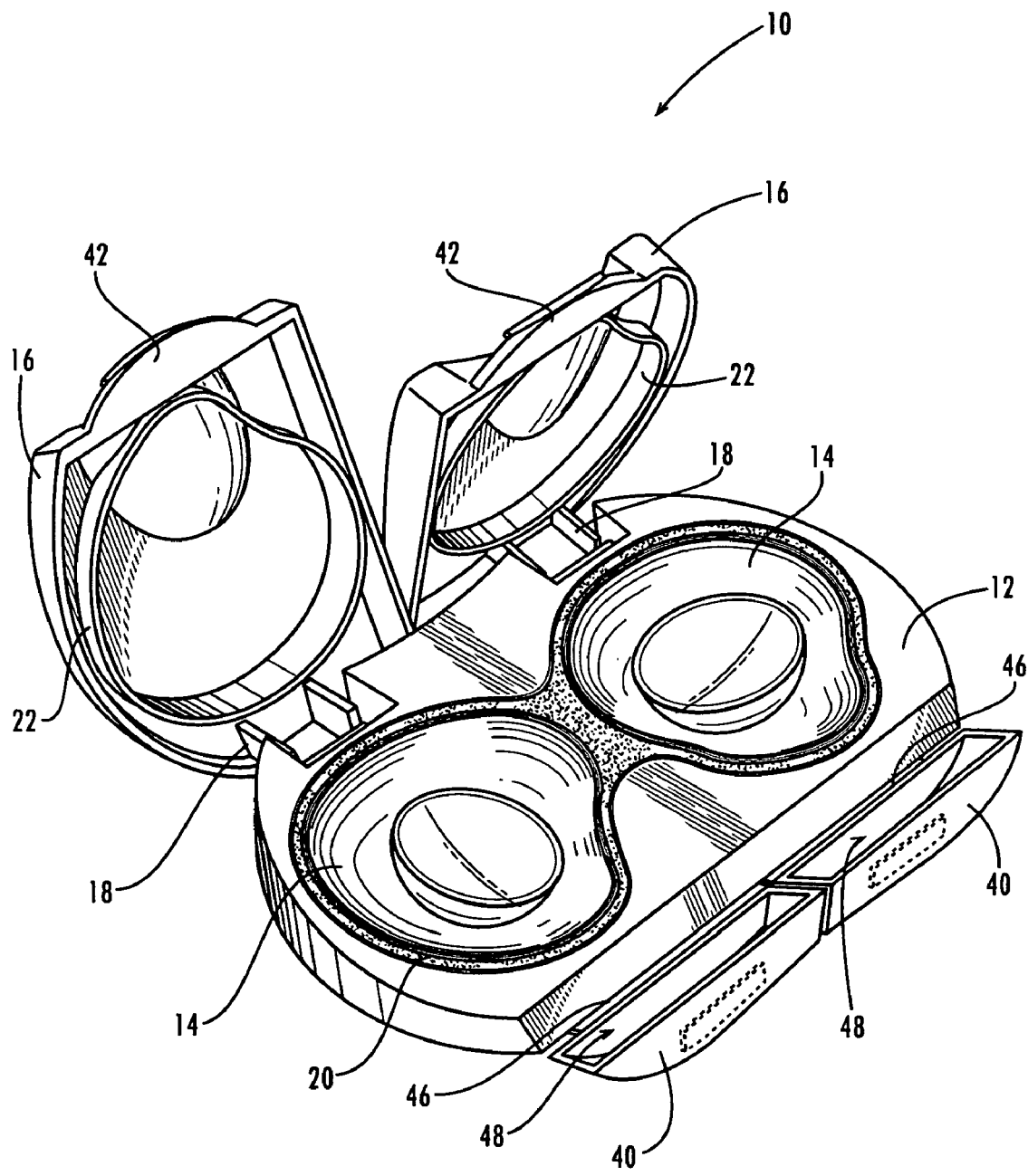
FIG. 3 shows the lens case of FIG. 1 in an open configuration.

The lens case 10 preferably further comprises at least one, and preferably two covers or caps 16, each cap adapted to close over one of the wells 14 to provide a substantially liquid-impermeable seal. In the depicted embodiment, two caps 16 are provided immediately adjacent to one another with directly confronting inner edges, so that each cap can be separately opened to access a contact lens in one of the wells 14 while a lens in the other well remains protected from contamination or spillage. In alternate embodiments, a single cover closes over both wells. Each cover or cap 16 is preferably hingedly mounted to the case main body 12 by a hinged connection 18, and adapted to be swung between an open position allowing access to the interior of the well 14 (FIG. 3), and a closed position covering the well and sealing its contents therein (FIGS. 1 and 2). The hinge mechanism optionally comprises a detent or catch to produce an audible or tactile click as the cover 16 moves into its closed position. Because the caps 16 are hingedly affixed to the base or body portion of the lens case 12, rather than being separably removable from the base, the caps are not subject to misplacement separate from the entire lens case. Also, because the caps 16 are connected to the base 12 at a fixed connection point, preferably at the rear edge of the lens case 10, the lens case is self-orienting. So long as the user positions the lens case 10 with the cap hinges 15 in a consistent orientation (typically facing away from the user) each time he or she uses the case, the left lens well will be on the user's left and the right lens well will be on the user's right. The case can be color coded, with the left lens well and/or cover being a different color than the right lens well and/or cover, to provide the user with further identification of the lens case's orientation.

The base 12 preferably defines a recess around the periphery of each well 14, within which recess one or more compressible gasket(s) 20 is/are provided. In the depicted embodiment, a single gasket 20 surrounds the periphery of each well 14, and in alternate embodiments a separate gasket surrounds each well. The gasket 20 can be formed as a separate component and attached to the base 12, as by adhesive, solvent bonding or thermal welding; or it can be molded together with the base of a different material, as by using a two-shot co-molding process. An upright flange or fin 22 having a peripheral outline corresponding to, but slightly larger than, the outer periphery of the underlying well 14 preferably projects downwardly from the underside of each cap 16, forming a contact surface in continuous compressive contact with the gasket 20 to seal against leakage when the cap is closed.

Figure 4:
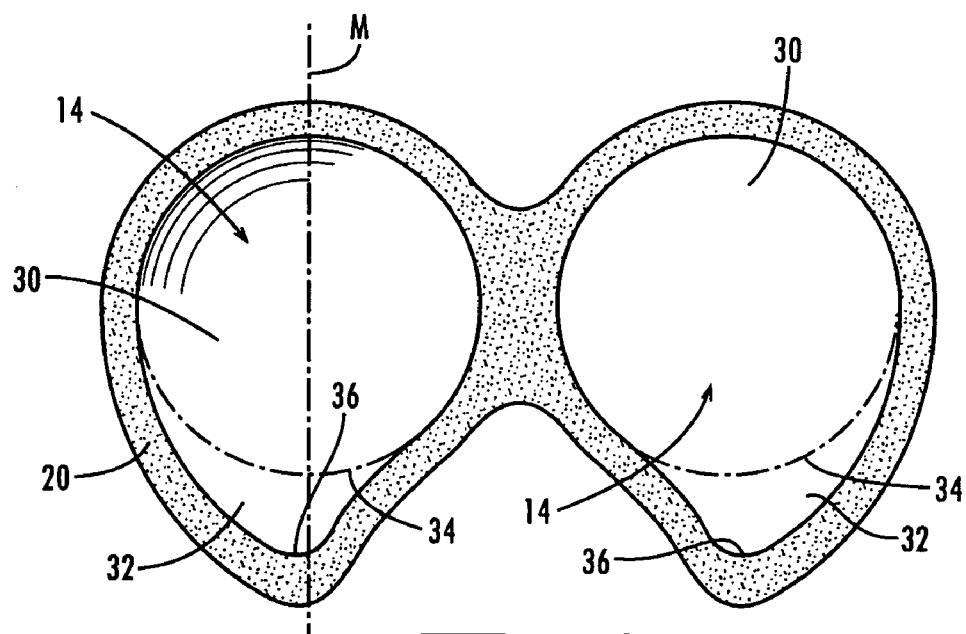
FIG. 4 is a top view showing the profile of the lens wells and gasket portions of the lens case of FIG. 1.

FIG. 4 better shows the profile of the well portions 14 of the lens case 10, according to an example embodiment of the invention. Each well 14 preferably comprises two portions that make a continuous and smooth transition into one another. The first portion of the well 14 is a substantially hemispherical primary well or bowl portion 30, the dimensions of which are so chosen that it can accommodate contact lenses of virtually all current sizes, but is not substantially larger in diameter than such lenses. A practical value for the diameter of the main bowl portion 30 measured in the plane of the well opening is, for example, approximately 20-30 mm, most preferably about 25 mm; and a practical value for the depth of the main well portion measured with respect to the plane of the well opening in the top surface of the base is approximately 6-15 mm, most preferably about 11 mm. The second portion of the well 14 is a secondary or extension well portion 32, the shape of which can best be compared to that of a tapering or funnel-shaped channel that becomes continuously narrower, shallower and flatter in the direction away from the main well portion 30. The secondary well portion 32 adjoins and extends from the side of the main well portion 30 and, as already mentioned, makes a smooth transition into the latter. The broken profile line 34 depicted in FIG. 4 marks the transition between the two well portions for purposes of description, but is an imaginary line that is not detectable in reality due to the smooth transition between well portions. The depth of the secondary well portion 32 becomes progressively shallower toward its tip 36, preferably along a smoothly curved continuous surface that transitions from a concavely curved contour at the intersection with the main well 30 into a convexly curved contour proximal the tip 36. The geometrical spatial form of the secondary well 32 is such that the main well 30 and the secondary well 32 together, that is to say the overall outline of the well 14, has an asymmetrical raindrop or teardrop-shaped peripheral profile in the plane of the well opening. The tip 36 of the drop profile preferably lies approximately on the central or longitudinal axis M of the well 14. Owing to the teardrop shape of the contour of the well 14, the peripheral recess around the well 14 in which the gasket is disposed is also generally teardrop-shaped. In the depicted embodiment, the teardrop shaped wells 14 are oriented with their tips 36 directed away from the hinged connection 18 of the caps 16 to the base 12 (referred to herein as a 0° orientation), such that when the user positions the lens case with the hinged connection facing away from him or her, the user can remove lenses from the wells by sliding the lenses toward the user through the tips 36 of the wells. In alternate embodiments, the wells are oriented with their tips 36 directed outwardly toward the sides (a 90° orientation), so that the lenses are removed by sliding them sideways out of the wells. And in still other embodiments, the wells are oriented with their tips 36 directed at an oblique angle between the 0° orientation and the 90° orientation, or in some other orientation. The tear-drop shape of the well 14 permits a very simple and easy removal of the lens. The shape also conserves lens care solution, there being only an extremely small dead volume in the secondary well portion which is not occupied by the lens stored therein, so that only a small additional quantity of lens care solution is necessary to fill the well to a level sufficient for the reliable treatment and preservation of the lens.

The lens case 10 preferably further comprises a latch or closure member 40 for each cap or cover 16, which can be engaged or activated to positively secure the cover in its closed position, preferably with a single manual action. Each cap 16 preferably includes a flange 42 projecting from its free end opposite the hinge connection 18, and a recess or indentation 44 in its top surface adjacent the free end. Each indentation 44 preferably has a concave curvature approximately conforming the radius of curvature of a human fingertip or thumb, to provide ergonomic access for releasing the closure member, and for improved aesthetic appeal. The closure members 40 are preferably integrally formed with the base 12 as unitary moldings, and the closure members and base are pivotally joined to one another by integrally molded living hinges 46 formed of a section of material of reduced thickness relative to the base and closure member. Alternatively, the closure members 40 are formed as separate components, and are pivotally attached to the base 12 by hinge pins, snap couplings, or other pivotal connection means. The closure members 40 are pivotal between an engaged or latched position (shown in FIG. 1), and a disengaged or unlatched position (shown in FIG. 2). Each closure member 40 preferably comprises a recess 48 having a resilient fin 50 positioned therein for positive engagement with a lip formed on the flange 42 when the closure member is engaged to latch the cap 16 closed. Cooperative engagement between the flange 42 of the cap 16 and the fin 50 of the closure member 40 preferably provides an audible and/or tactile click when the snap-fitting therebetween is fully closed and engaged, and when it is disengaged and opened, to provide the user with sensory feedback indicating that a secure closure has been completed, and to avoid inadvertent opening and loss of contents. The closure member 40 preferably comprises a top panel that tapers downwardly toward its distal end opposite the point of contact with the cover 16, such that the height of the recess 48 becomes smaller toward the distal end. In this manner, contact against the flange 42 of the cover 16 by the inclined inner face of the top panel of the closure member 40 presses the cover down against the base 12 to engage the seal between the gasket 20 and the flange 22 as the closure member is pivoted into its latched position. Optionally, a drain hole is provided through the closure member 40, in communication with the recess 48, to permit any lens care solution overflowing into the recess to escape.

One or more legs or struts preferably extend from the bottom of the base 12 to support the lens case on a countertop or other supporting surface during use and to maintain the top surface of the base in a generally horizontal position as the covers 16 and closure members 18 are opened and closed. The legs or struts preferably support the base 12 a sufficient distance above the supporting surface to prevent the hinges 18 and the closure members 40 from contacting the supporting surface when opened and closed, which could cause the base to tip and spill the contents of the wells 14.

Figure 5:
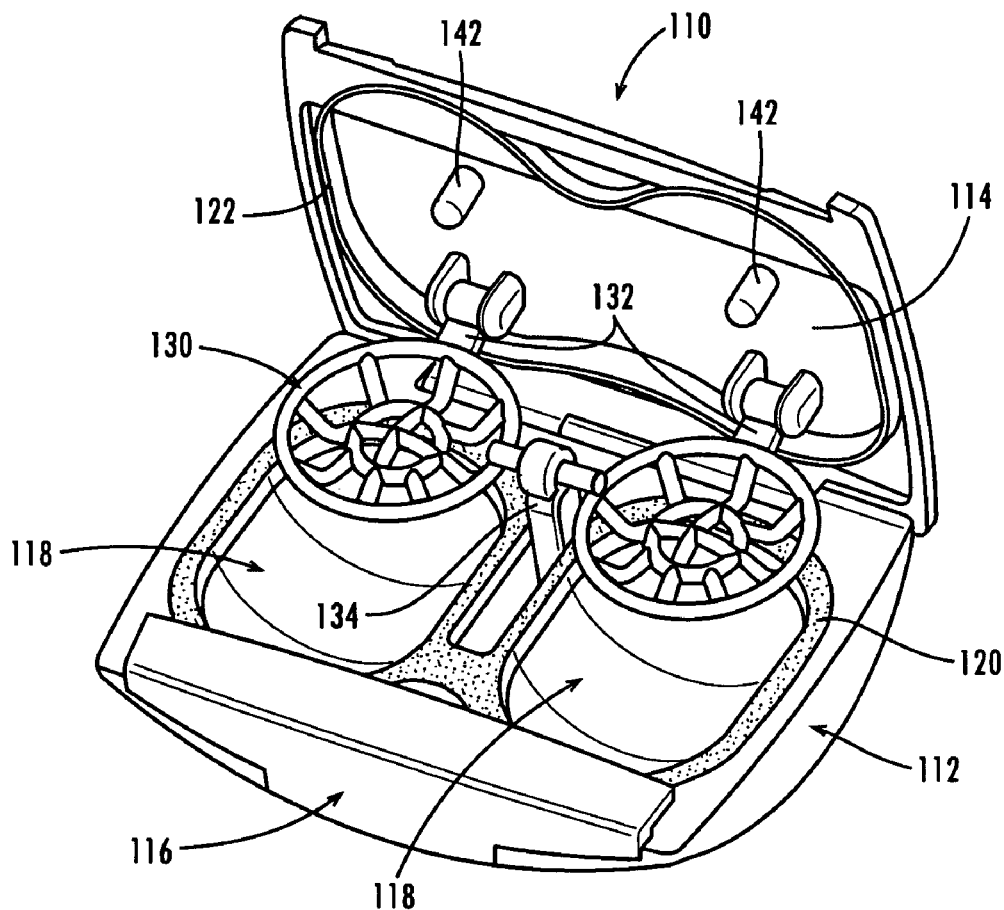
FIG. 5 shows a perspective view of a lens case according to another example embodiment of the present invention, shown in an open configuration.
Figure 6:
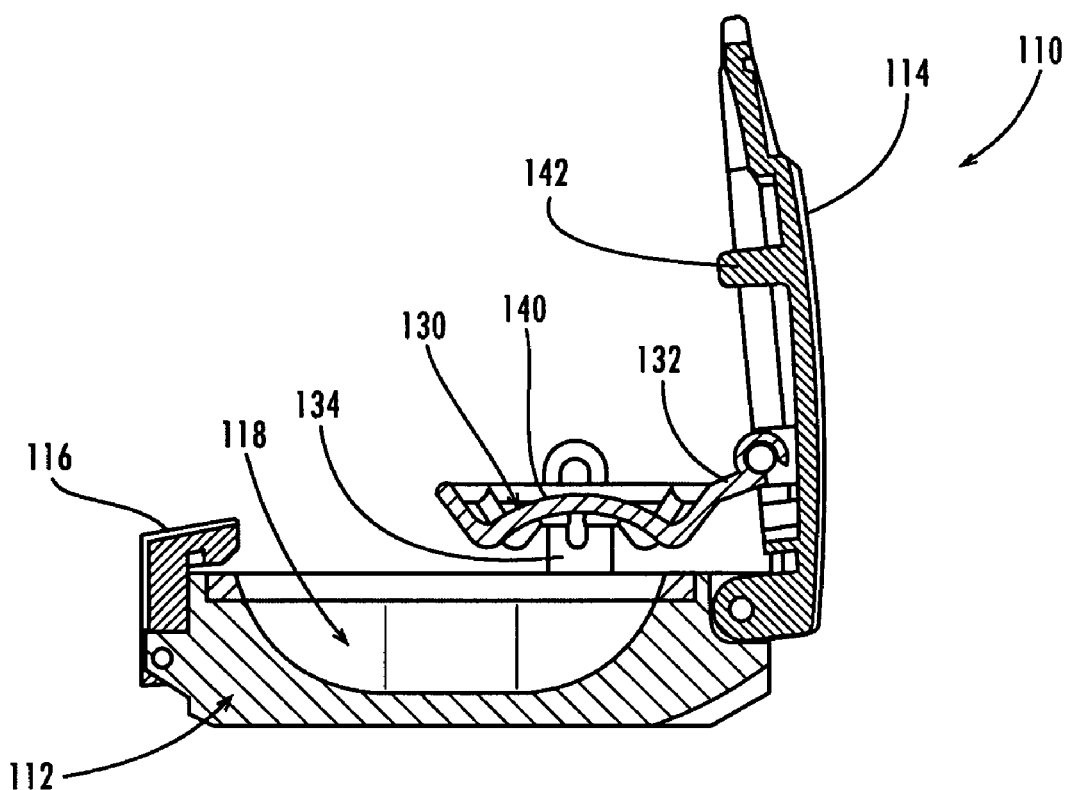
FIG. 6 is a side cross-sectional view of the lens case of FIG. 5.
Figure 7:
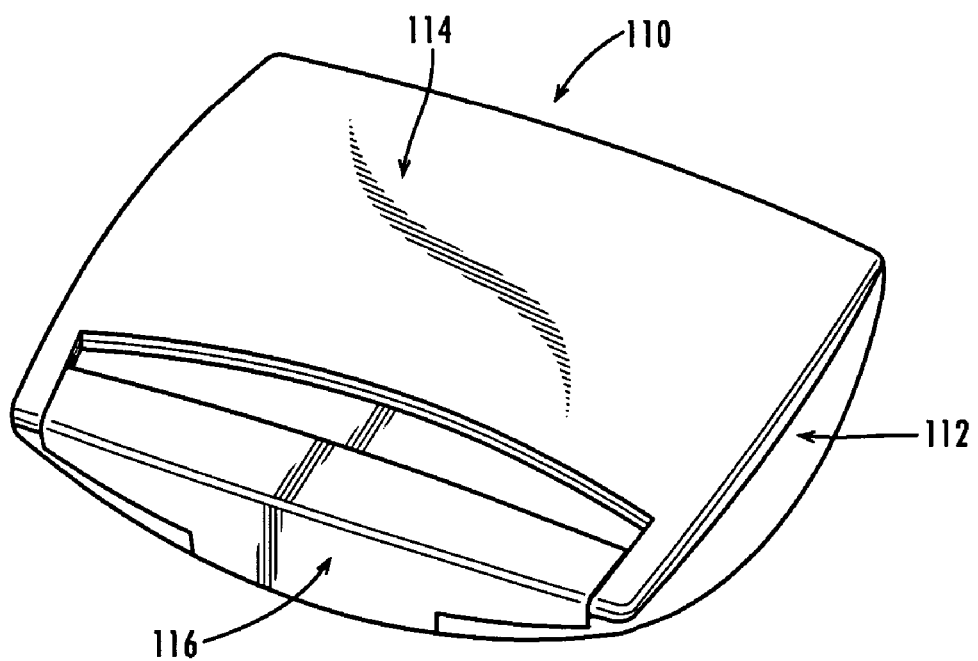
FIG. 7 shows the lens case of FIG. 5 in a closed configuration.

Referring now to FIGS. 5-7, another lens case embodiment according to the present invention is shown. Lens case 110 preferably includes an outer housing similar to that described above, comprising a base 112, at least one cover 114, and a latch or closure member 116 associated with each cover. The cover 114 is preferably hingedly connected to the base 112 and pivotal between a closed position (FIG. 7) encapsulating the case's contents and an open position (FIG. 5) allowing access to the case's interior. The latch 116 is preferably hingedly connected to the base 112 and pivotal between an engaged position (FIG. 7) to positively retain the cover 114 closed, and a disengaged position (FIG. 5) permitting the cover to be opened. At least one, and preferably a pair of wells 118 is/are formed in the base 112, for containing lens care solution. A compressible gasket 120 preferably surrounds each well 118, and a flange 122 extends downwardly from the inner face of the cover 114 to form a liquid-impermeable seal against the gasket when the cover is closed.

The lens case 110 preferably further comprises one or more lens carriers 130 for holding contact lenses and lowering and raising them into and out of the lens care solution in the wells 118. In the depicted embodiment, a pair of lens carriers 130 are adjoined to one another by an intermediate connector bar; but in alternate embodiments of the invention a pair of separate unconnected lens carriers, or a single elongate lens carrier, are provided. The lens carriers 130 are preferably affixed to the cover 114 by a first connector link 132, and to the base 112 by a second connector link 134. Pin connections between the connector links 132, 134, the base 112, the cover 114 and the lens carriers 130 permit relative pivotal motion between the elements in the manner of a four-bar-linkage, causing the lens carriers to be raised out of the well 118 as the cover is opened, and lowered into the well as the cover is closed, and maintaining the lens carriers 130 in a consistent generally horizontal orientation (i.e., parallel to the upper surface of the base 112) throughout their range of motion as they are raised and lowered.

Each lens carrier 130 is preferably porous to permit circulation of the lens care solution throughout the well and into contact with the entire anterior and posterior surfaces of the lens. For example, the lens carrier 130 may be a mesh-like member, such as a basket. The basket preferably has a quasi-hemispherical shape with upwardly directed sidewall portions and an upwardly extending convex central bottom portion 140 for supporting the posterior surface (concave surface) of a contact lens. This basket configuration advantageously allows the user to conveniently place a contact lens removed from the eye directly onto the carrier without manipulation that could lead to loss of the lens, since when a contact lens is removed from an eye, the anterior surface (convex surface) of the contact lens typically rests against the user's finger. Thus, the user can readily deposit a removed lens directly in the basket by simply placing the posterior surface of the lens against the convex surface 140 of the basket bottom.

In preferred forms, the basket 130 presents a minimized contact surface with the contact lens to be stored therein, to minimize lens adhesion to the carrier and maximize lens contact with the lens care solution. For example, it is advantageous to provide the basket 130 with an open lattice structure, which has an upper lens-contacting face and an opposite lower side that does not contact the lens, wherein the lens-contacting side of the lattice has relatively sharp edges that contact the lens. In a preferred embodiment, the sharp edges present thin lines of contact, for example having a contact edge thickness of about $1/10$ mm or less. Similar baskets are detailed in commonly assigned co-pending U.S. patent application Ser. No. 10/152,930 filed May 22, 2002, incorporated herein by reference in its entirety.

The lens case 110 preferably further comprises one or more (two are shown) anchoring members 142 projecting downward from the inner face of the cover 114 to maintain a contact lens in a stable position against the lens carrier 130, and to ensure that the lens is fully immersed in solution within the well 118 when the cover is closed. In example embodiments, each lens anchoring means is a post or stake having a free end with a relatively small surface area for contacting the lens. Alternatively, the lens anchoring member comprises a porous surface to permit circulation of a lens care solution therethrough and into contact with the entire surface of the lens. For example, the lens anchoring means may be an open-latticed mesh-like member, such as a hemisphere-shaped basket with its open end attached to one of the caps, and having a surface profile that is complementary to that of the basket forming the lens carrier 130 such that the lens is held submerged between the two basket members.

Figure 8:
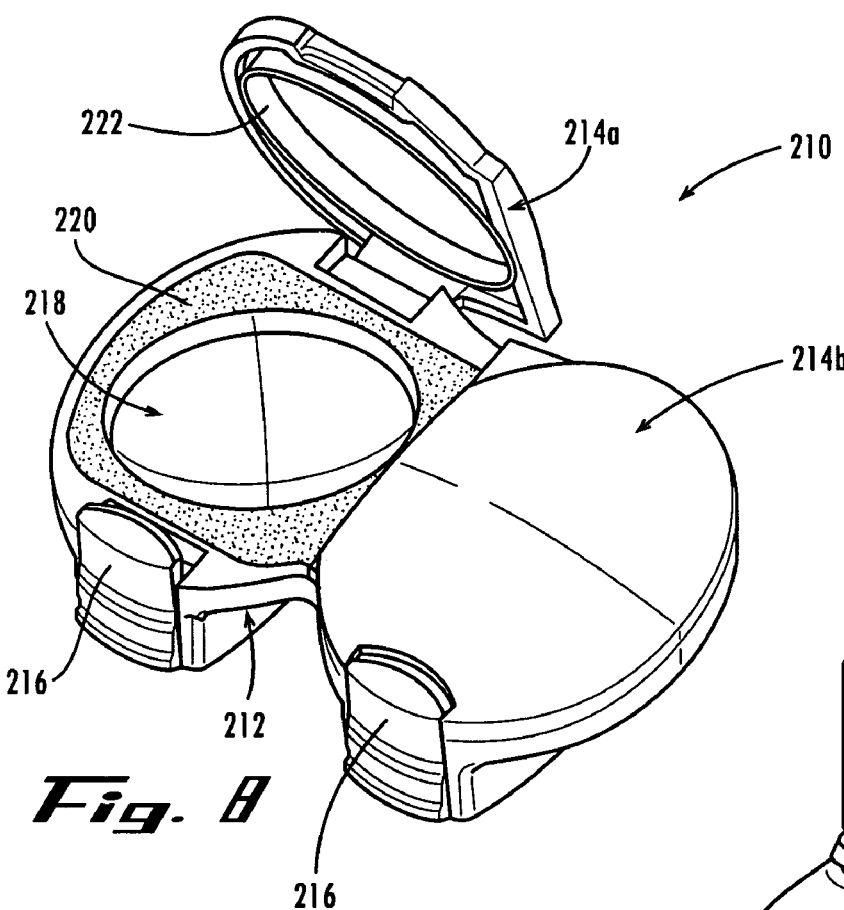
FIG. 8 shows a perspective view of a lens case according to yet another example embodiment of the present invention.

FIG. 8 shows another embodiment of a lens case 210 according to the present invention. Lens case 210 preferably includes an outer housing similar to that described above, comprising a base 212, at least one cover 214 (two covers 214a, 214b are provided in the depicted embodiment), and a latch or closure member 216 associated with each cover. The covers 214a, 214b are preferably hingedly connected to the base 212 and pivotal between a closed position (214b) and an open position (214a) allowing access to the case's interior. Each latch 216 is preferably pivotally connected to the base 212 and is resiliently biased toward a latched or engaged position to positively retain the cover 214 closed. Pressing inwardly against a lower portion of the latch 216 preferably causes an upper portion of the latch to toggle outwardly into an unlatched position, releasing the cover 214 and allowing it to be opened. At least one, and preferably a pair of wells 218 is/are formed in the base 212, for containing a lens and a quantity of lens care solution. A compressible gasket 220 preferably surrounds each well 218, and a flange 222 extends downwardly from the inner face of each cover 214 to form a liquid-impermeable seal against the gasket when the cover is closed.

Figure 9:
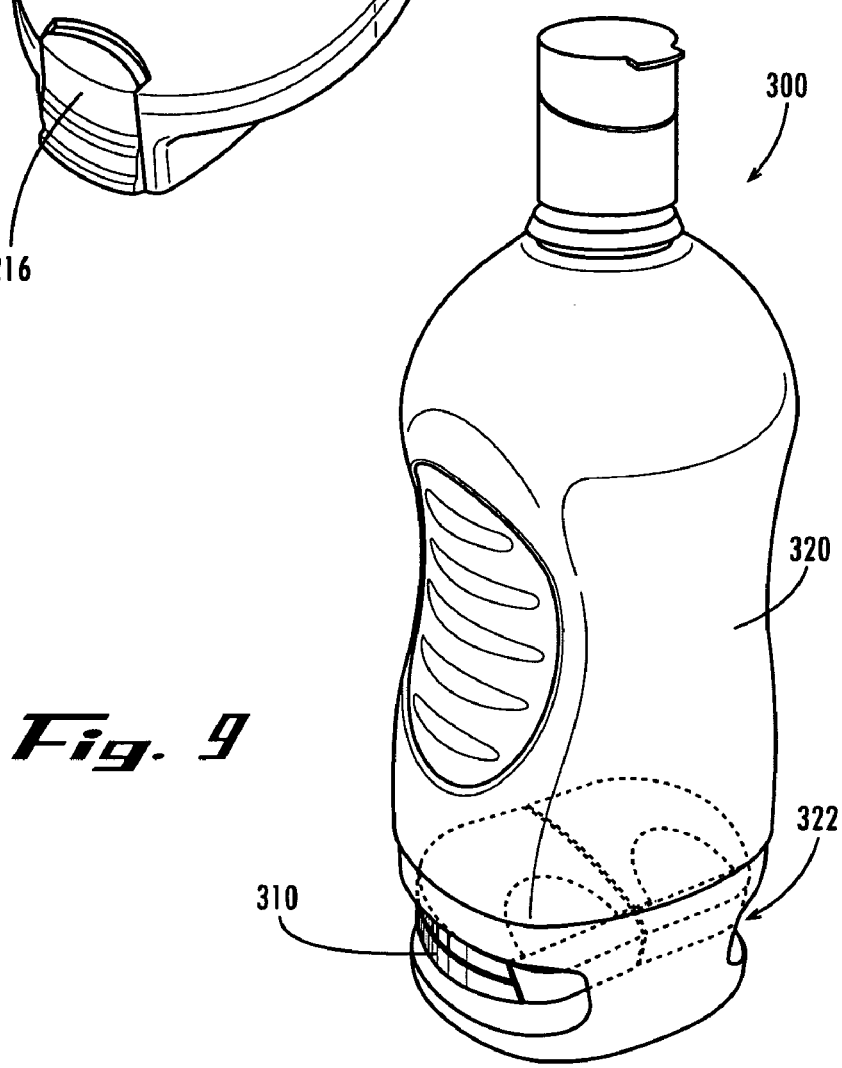
FIG. 9 shows a perspective view of a lens care system incorporating a lens case according to an example embodiment of the present invention.

With reference now to FIG. 9, the present invention, in another aspect, provides a lens case for use in combination with associated components of an integrated lens care system 300. The primary components of the system 300 include a lens case 310 substantially as described herein, and a solution dispensing container 320 having an openly accessible docking site 322, wherein the lens case is releasably secured to the container in or on its docking site. Concurrently filed U.S. patent application Ser. No. (Attorney Docket No. LP/V-33425A/CVA), incorporated herein by reference in its entirety, discloses additional details and embodiments regarding the system and the container. In preferred form, the docking site 322 comprises a resilient raised rib, panel, finger or other retainer element(s), which interengage with a cooperating recess, protrusion or other surface feature(s) of the lens case 310 to retain the lens case within the docking site and to permit the retainer element to resiliently engage and disengage the lens case as it is inserted into and removed from the docking site. In example embodiments, the retainer element positively engages and disengages the lens case 310 with an audible or tactile click or other sensory indicator to confirm engagement and disengagement to the user.

Although various embodiments of the invention have been described using specific terms, devices, and methods, such description is for illustrative purposes only. The words used are words of description rather than of limitation. It is to be understood that changes and variations may be made by those skilled in the art without departing from the spirit or scope of the present invention, which is set forth in the following claims. In addition, it should be understood that aspects of the various embodiments may be interchanged either in whole or in part, and that individual elements of the invention may have separate utility in addition to utility in combination with the other elements as described. Furthermore, titles, headings, the abstract, or the like are provided to enhance the reader's comprehension of this document, and should not be read as limiting the scope of the present invention. Accordingly, the spirit and scope of the appended claims should not be limited to the description of the specific example embodiments contained therein.

What is claimed is:

1. A contact lens case comprising:
   a base portion defining at least one well for receiving a contact lens and a quantity of lens care solution,
   at least one cover hingedly connected to the base portion and movable between an open position allowing access to the at least one well and a closed position overlying the at least one well,
   a latch selectively engageable with a portion of the at least one cover to retain the cover in its closed position, wherein each of the at least one cover comprises a generally concave indentation adjacent the latch; and
   a lens carrier for supporting a contact lens during immersion in the well.

2. The contact lens case of claim 1, wherein the base portion comprises a compressible gasket surrounding the well, and the cover comprises a flange projecting from a lower face thereof for sealing engagement with the gasket when the cover is in its closed position.

3. The contact lens case of claim 1, wherein the latch is pivotally connected to the base portion.

4. The contact lens case of claim 3, wherein the latch and the base portion comprise a unitary molding joined by a living hinge.

5. The contact lens case of claim 3, wherein the latch comprises an inclined contact face for urging the cover into its closed position as the latch is engaged.

6. The contact lens case of claim 1, wherein the lens carrier moves between a lowered position wherein the contact lens is immersed in the well, and a raised position wherein the contact lens is above the well.

7. The contact lens case of claim 6, wherein the lens carrier is connected to the cover by a first connector link, so that the lens carrier moves to its lowered position when the cover is in its closed position, and the lens carrier moves to its raised position when the cover is in its open position.

8. The contact lens case of claim 7, wherein the lens carrier is connected to the base by a second connector link, so that the lens carrier is maintained in an orientation generally parallel to the base as the lens carrier moves between its lowered position and its raised position.

9. The contact lens case of claim 1, wherein the lens carrier is generally concave with upwardly directed sidewall portions and a convex central portion for supporting the posterior surface of a contact lens placed thereon.

10. The contact lens case of claim 1, further comprising an anchoring member on an inner face of the cover for holding the contact lens in place against the lens carrier.

11. The contact lens case of claim 1, wherein the at least one well comprises separate first and second wells recessed into the base portion.

12. The contact lens case of claim 11, wherein the at least one cover comprises first and second covers hingedly connected to the base portion, each cover independently operable to cover and uncover one of said first and second wells.

13. The contact lens case of claim 1, in combination with a lens solution dispensing container having a docking site, said contact lens case being releasably engageable with the docking site of the container.

14. A contact lens case comprising a base with a well formed therein, a cover hingedly attached to the base and pivotal between an open position exposing the well and a closed position covering the well, a gasket between the base and the cover forming a fluid-impermeable seal around the well when the cover is in its closed position, and a latch for securing the cover in its closed position, and wherein the cover comprises a generally concave indentation adjacent the latch.

15. The contact lens case of claim 14, wherein the gasket is attached to the base around the well, and wherein the cover comprises a flange for contact against the gasket.

16. The contact lens case of claim 14, wherein engagement of the latch compresses the cover against the base to form the fluid-impermeable seal around the well.

17. The contact lens case of claim 14, in combination with a lens solution dispensing container having a docking site, said contact lens case being releasably engageable with the docking site of the container.

\* \* \* \* \*